US009364276B2

(12) United States Patent
Graf et al.

(10) Patent No.: US 9,364,276 B2
(45) Date of Patent: Jun. 14, 2016

(54) TISSUE GRAFT ANCHOR ASSEMBLY AND INSTRUMENTATION FOR USE THEREWITH

(71) Applicant: Smith & Nephew, Inc., Memphis, TN (US)

(72) Inventors: Ben K. Graf, Madison, WI (US); Alfred R. Berube, North Attleboro, MA (US); Gary M. McCarthy, East Bridgewater, MA (US)

(73) Assignee: Smith & Nephew, Inc, Memphis, TN (US)

( * ) Notice: Subject to any disclaimer, the term of this patent is extended or adjusted under 35 U.S.C. 154(b) by 0 days.

(21) Appl. No.: 14/185,435

(22) Filed: Feb. 20, 2014

(65) Prior Publication Data

US 2014/0236183 A1 Aug. 21, 2014

Related U.S. Application Data

(62) Division of application No. 12/832,616, filed on Jul. 8, 2010, now Pat. No. 8,663,325.

(60) Provisional application No. 61/224,123, filed on Jul. 9, 2009, provisional application No. 61/225,240, filed on (Continued)

(51) Int. Cl.
*A61B 17/88* (2006.01)
*A61F 2/08* (2006.01)
(Continued)

(52) U.S. Cl.
CPC ........... *A61B 17/8869* (2013.01); *A61B 17/068* (2013.01); *A61B 17/0642* (2013.01);
(Continued)

(58) Field of Classification Search
CPC ............. A61B 17/0642; A61B 17/068; A61B 17/8869; A61B 17/0482; A61F 2/0811; A61F 2002/0835; A61F 2002/0841; A61F 2002/0864

USPC .............. 606/103, 74, 139–150, 113; 84/267, 84/297 R; 24/69 R, 115 R, 133, 134 R; 263/13.13, 2.11

See application file for complete search history.

(56) References Cited

U.S. PATENT DOCUMENTS 2,490,364 A   12/1949  Livingston
3,896,504 A   7/1975   Fischer
(Continued)

FOREIGN PATENT DOCUMENTS

EP   1261298 B1   3/2001
EP   1263329 B1   3/2001
(Continued)

OTHER PUBLICATIONS

Australian Examination Report No. 1; Application No. 2010271431, mailed Dec. 3, 2014.
(Continued)

*Primary Examiner* — Pedro Philogene
(74) *Attorney, Agent, or Firm* — Burns & Levinson LLP; Joseph M. Marala

(57) ABSTRACT

The present disclosure relates to a soft tissue graft anchor. The anchor includes a plurality of prongs, each prong including a distal end and a proximal end, wherein the prongs are coupled at their distal ends to form an inner cavity having an opening, at least one of the prongs including a fin, the fin extending perpendicular to a longitudinal axis of the prong and including a pointed end. A tissue graft anchor assembly, a method for tissue repair, and instrumentation for use therewith are also disclosed.

20 Claims, 20 Drawing Sheets

Related U.S. Application Data

Jul. 14, 2009, provisional application No. 61/312,506, filed on Mar. 10, 2010, provisional application No. 61/315,521, filed on Mar. 19, 2010, provisional application No. 61/332,998, filed on May 10, 2010.

(51) Int. Cl.
*A61B 17/064* (2006.01)
*A61B 17/068* (2006.01)
*A61B 17/04* (2006.01)

(52) U.S. Cl.
CPC .......... *A61F2/0811* (2013.01); *A61B 17/0482* (2013.01); *A61F 2002/0835* (2013.01); *A61F 2002/0841* (2013.01); *A61F 2002/0864* (2013.01)

(56) References Cited

U.S. PATENT DOCUMENTS

| | | | |
|---|---|---|---|
| 4,011,602 A | 3/1977 | Rybicki et al. | |
| 4,760,843 A | 8/1988 | Fischer et al. | |
| 5,037,422 A | 8/1991 | Hayhurst et al. | |
| 5,041,118 A | 8/1991 | Wasilewski | |
| 5,084,050 A | 1/1992 | Draenert | |
| 5,129,902 A | 7/1992 | Goble et al. | |
| 5,152,790 A | 10/1992 | Rosenberg et al. | |
| 5,236,445 A | 8/1993 | Hayhurst et al. | |
| 5,312,410 A * | 5/1994 | Miller et al. | 606/86 R |
| 5,423,860 A | 6/1995 | Lizardi et al. | |
| 5,464,427 A | 11/1995 | Curtis et al. | |
| 5,472,452 A | 12/1995 | Trott | |
| 5,486,197 A | 1/1996 | Le et al. | |
| 5,531,792 A | 7/1996 | Huene | |
| 5,584,835 A | 12/1996 | Greenfield | |
| 5,601,557 A | 2/1997 | Hayhurst | |
| 5,632,748 A | 5/1997 | Beck, Jr. et al. | |
| 5,643,320 A | 7/1997 | Lower et al. | |
| 5,643,321 A | 7/1997 | McDevitt | |
| 5,645,589 A | 7/1997 | Li | |
| 5,647,874 A | 7/1997 | Hayhurst | |
| 5,702,398 A | 12/1997 | Tarabishy | |
| 5,707,395 A | 1/1998 | Li | |
| 5,720,753 A | 2/1998 | Sander et al. | |
| 5,725,529 A | 3/1998 | Nicholson et al. | |
| 5,733,307 A | 3/1998 | Dinsdale | |
| 5,782,865 A | 7/1998 | Grotz | |
| 5,840,078 A | 11/1998 | Yerys | |
| 5,911,721 A | 6/1999 | Nicholson et al. | |
| RE36,289 E | 8/1999 | Le et al. | |
| 5,935,129 A | 8/1999 | McDevitt et al. | |
| 5,957,953 A | 9/1999 | DiPoto et al. | |
| 5,961,538 A | 10/1999 | Pedlick et al. | |
| 5,968,078 A | 10/1999 | Grotz | |
| 6,022,373 A | 2/2000 | Li | |
| 6,024,758 A | 2/2000 | Thai | |
| 6,045,574 A | 4/2000 | Thai | |
| 6,123,711 A | 9/2000 | Winters | |
| 6,146,406 A | 11/2000 | Shluzas et al. | |
| 6,149,669 A | 11/2000 | Li | |
| 6,152,928 A | 11/2000 | Wenstrom, Jr. | |
| 6,162,234 A | 12/2000 | Freedland et al. | |
| 6,248,062 B1 | 6/2001 | Adler et al. | |
| RE37,963 E | 1/2003 | Thal | |
| 6,508,830 B2 | 1/2003 | Steiner | |
| 6,517,542 B1 | 2/2003 | Papay et al. | |
| 6,527,795 B1 | 3/2003 | Lizardi | |
| 6,544,267 B1 | 4/2003 | Cole et al. | |
| 6,547,778 B1 * | 4/2003 | Sklar et al. | 606/1 |
| 6,554,862 B2 | 4/2003 | Hays et al. | |
| 6,575,976 B2 | 6/2003 | Grafton | |
| 6,635,073 B2 | 10/2003 | Bonutti | |
| 7,008,451 B2 | 3/2006 | Justin et al. | |
| 7,172,595 B1 | 2/2007 | Goble | |
| 7,235,100 B2 | 6/2007 | Martinek | |
| 7,309,355 B2 | 12/2007 | Donnelly et al. | |
| 7,491,217 B1 | 2/2009 | Hendren et al. | |
| 7,601,155 B2 | 10/2009 | Petersen | |
| 7,651,528 B2 | 1/2010 | Montgomery et al. | |
| 7,828,848 B2 | 11/2010 | Chauvin et al. | |
| 7,837,731 B2 | 11/2010 | Sklar | |
| 7,867,251 B2 | 1/2011 | Colleran et al. | |
| 7,875,056 B2 | 1/2011 | Jervis et al. | |
| 7,879,036 B2 | 2/2011 | Biedermann et al. | |
| 7,879,094 B2 | 2/2011 | Baird et al. | |
| 7,887,551 B2 | 2/2011 | Bojarski et al. | |
| 7,951,198 B2 | 5/2011 | Sucec et al. | |
| 7,955,388 B2 | 6/2011 | Jensen et al. | |
| 7,967,861 B2 | 6/2011 | Montgomery et al. | |
| 8,057,524 B2 | 11/2011 | Meridew | |
| 8,066,713 B2 | 11/2011 | DiMauro et al. | |
| 8,100,969 B2 | 1/2012 | Hart | |
| 8,110,001 B2 | 2/2012 | Carter et al. | |
| 8,128,658 B2 | 3/2012 | Kaiser et al. | |
| 8,192,490 B2 | 6/2012 | Baird et al. | |
| 8,226,714 B2 | 7/2012 | Beck, Jr. et al. | |
| 8,226,716 B2 | 7/2012 | Mckernan et al. | |
| 8,298,285 B2 | 10/2012 | Sklar et al. | |
| 8,317,863 B2 | 11/2012 | Cauldwell et al. | |
| 8,414,647 B2 | 4/2013 | Bard et al. | |
| 8,435,293 B2 | 5/2013 | Donnelly et al. | |
| 8,470,036 B2 | 6/2013 | Barnes et al. | |
| 8,470,037 B2 | 6/2013 | Re et al. | |
| 8,491,652 B2 | 7/2013 | Fening et al. | |
| 8,523,902 B2 | 9/2013 | Heaven et al. | |
| 8,535,377 B2 | 9/2013 | Myers et al. | |
| 8,545,535 B2 | 10/2013 | Hirotsuka et al. | |
| 8,663,279 B2 | 3/2014 | Burkhart et al. | |
| 8,663,325 B2 | 3/2014 | Graf et al. | |
| 8,688,232 B2 | 4/2014 | Finley et al. | |
| 8,747,469 B2 | 6/2014 | Wang et al. | |
| 8,747,470 B2 | 6/2014 | Beck, Jr. et al. | |
| 8,771,352 B2 * | 7/2014 | Conner et al. | 623/13.13 |
| 8,778,023 B2 | 7/2014 | Sklar | |
| 8,784,295 B2 | 7/2014 | Rocheleau et al. | |
| 8,808,374 B2 | 8/2014 | Eggli | |
| 2001/0049529 A1 | 12/2001 | Cachia et al. | |
| 2002/0007182 A1 | 1/2002 | Kim | |
| 2002/0040241 A1 | 4/2002 | Jarninen | |
| 2002/0072797 A1 | 6/2002 | Hays et al. | |
| 2002/0161401 A1 | 10/2002 | Steiner | |
| 2003/0065361 A1 | 4/2003 | Dreyfuss | |
| 2003/0088272 A1 | 5/2003 | Smith | |
| 2003/0105489 A1 | 6/2003 | Eichhorn et al. | |
| 2003/0105524 A1 | 6/2003 | Paulos et al. | |
| 2003/0187446 A1 | 10/2003 | Overaker et al. | |
| 2003/0233095 A1 | 12/2003 | Urbanski et al. | |
| 2004/0111117 A1 | 6/2004 | Colleran et al. | |
| 2004/0133239 A1 | 7/2004 | Singhata | |
| 2004/0153076 A1 | 8/2004 | Singhatat et al. | |
| 2004/0193285 A1 | 9/2004 | Roller et al. | |
| 2004/0230194 A1 | 11/2004 | Urbanski et al. | |
| 2004/0249384 A1 | 12/2004 | Blaha et al. | |
| 2004/0267266 A1 | 12/2004 | Daniels et al. | |
| 2004/0267361 A1 | 12/2004 | Donnelly et al. | |
| 2005/0055027 A1 | 3/2005 | Yeung et al. | |
| 2005/0234463 A1 | 10/2005 | Hershberger et al. | |
| 2006/0116719 A1 | 6/2006 | Martinek | |
| 2006/0149258 A1 | 7/2006 | Sousa | |
| 2007/0055255 A1 | 3/2007 | Siegel | |
| 2007/0156153 A1 | 7/2007 | Jiang et al. | |
| 2007/0225805 A1 | 9/2007 | Schmieding | |
| 2007/0233127 A1 | 10/2007 | Tuke et al. | |
| 2007/0233151 A1 | 10/2007 | Chudik | |
| 2008/0033549 A1 * | 2/2008 | Marshall et al. | 623/13.13 |
| 2008/0133007 A1 | 6/2008 | Donnelly et al. | |
| 2008/0154314 A1 | 6/2008 | McDevitt | |
| 2008/0161864 A1 | 7/2008 | Beck, Jr. et al. | |
| 2008/0183290 A1 | 7/2008 | Baird et al. | |
| 2008/0275554 A1 | 11/2008 | Iannarone et al. | |
| 2008/0288070 A1 | 11/2008 | Lo | |
| 2008/0319546 A1 | 12/2008 | Bojarski et al. | |
| 2009/0012522 A1 | 1/2009 | Lob | |
| 2009/0082821 A1 * | 3/2009 | Konno et al. | 606/86 A |

(56) References Cited

U.S. PATENT DOCUMENTS

| | | |
|---|---|---|
| 2009/0093850 A1 | 4/2009 | Richard |
| 2009/0216326 A1 | 8/2009 | Hirpara et al. |
| 2010/0016893 A1 | 1/2010 | Fanton |
| 2010/0049258 A1 | 2/2010 | Dougherty |
| 2010/0063541 A1 | 3/2010 | Brunelle et al. |
| 2010/0063542 A1 | 3/2010 | van der Burg et al. |
| 2010/0161055 A1 | 6/2010 | Donnelly et al. |
| 2010/0174369 A1 | 7/2010 | Wang et al. |
| 2010/0198258 A1 | 8/2010 | Heaven et al. |
| 2010/0217389 A1 | 8/2010 | Cheng et al. |
| 2010/0262184 A1 | 10/2010 | Dreyfuss |
| 2011/0009885 A1 | 1/2011 | Graf et al. |
| 2011/0112537 A1* | 5/2011 | Bernstein et al. ............... 606/74 |
| 2011/0112641 A1 | 5/2011 | Justin et al. |
| 2011/0144766 A1 | 6/2011 | Kale et al. |
| 2011/0184516 A1 | 7/2011 | Baird et al. |
| 2011/0184517 A1 | 7/2011 | Baird et al. |
| 2011/0196490 A1 | 8/2011 | Gadikota et al. |
| 2011/0251688 A1 | 10/2011 | Sklar |
| 2011/0282449 A1 | 11/2011 | Montgomery et al. |
| 2011/0313453 A1 | 12/2011 | Krumme et al. |
| 2012/0065677 A1 | 3/2012 | West, Jr. |
| 2012/0078298 A1 | 3/2012 | Sklar |
| 2012/0265299 A1 | 10/2012 | Beck, Jr. et al. |
| 2013/0138152 A1 | 5/2013 | Stone et al. |
| 2013/0144334 A1 | 6/2013 | Bouduban et al. |
| 2013/0150885 A1 | 6/2013 | Dreyfuss |
| 2013/0261677 A1 | 10/2013 | Bouduban et al. |
| 2014/0052179 A1 | 2/2014 | Dreyfuss et al. |
| 2014/0171983 A1 | 6/2014 | Graf et al. |
| 2014/0236183 A1 | 8/2014 | Graf et al. |
| 2014/0236231 A1 | 8/2014 | Graf et al. |
| 2014/0243978 A1 | 8/2014 | Beck, Jr. et al. |

FOREIGN PATENT DOCUMENTS

| | | |
|---|---|---|
| EP | 1199035 A1 | 4/2002 |
| EP | 1297799 A2 | 9/2002 |
| EP | 1491162 A1 | 12/2004 |
| EP | 1836996 A1 | 3/2006 |
| EP | 1905385 A2 | 4/2008 |
| FR | 2671717 A1 | 7/1992 |
| WO | WO0149190 A1 | 7/2001 |
| WO | WO0230262 A2 | 4/2002 |
| WO | 2007109280 A2 | 9/2007 |
| WO | 2008004057 A2 | 1/2008 |
| WO | 2008070186 A2 | 6/2008 |

OTHER PUBLICATIONS

Notice of Reasons for Rejection; Japanese Appln. No. 2102-519730; mailed Mar. 17, 2014.

International Search Report and Written Opinion for International Application No. PCT/US2012/029390, mailed Aug. 28, 2012.

* cited by examiner

TISSUE GRAFT ANCHOR ASSEMBLY AND INSTRUMENTATION FOR USE THEREWITH

CROSS-REFERENCE TO RELATED APPLICATIONS

This application claims the benefit of U.S. Patent Application No. 61/224,123, filed Jul. 9, 2009; U.S. Patent Application No. 61/225,240, filed Jul. 14, 2009; U.S. Patent Application No. 61/312,506, filed Mar. 10, 2010; U.S. Patent Application No. 61/315,521, filed Mar. 19, 2010; and U.S. Patent Application No. 61/332,998, filed May 10, 2010, the disclosures of which are incorporated by reference in their entireties.

BACKGROUND

1. Field of Technology

The present disclosure relates to the fixation of soft tissue to bone.

2. Related Art

In many aspects of orthopedic surgery it is necessary to fix a soft tissue to bone. In one example, a ligament, such as an anterior cruciate ligament (ACL), that has ruptured and is non-repairable, may be replaced by a soft tissue graft. The tissue graft can be harvested from various sites including, without limitation, the patellar tendon, quadriceps tendon, semitendonosis tendon, gracilis tendon, or a combination thereof. Alternatively, the graft may be formed from synthetic materials or from a combination of synthetic and natural materials.

The replacement tissue graft is implanted by securing one end of the tissue graft through a passage formed in the femur, and the other end of the graft through a passage formed in the tibia. Generally, an anchor (e.g., an interference screw or a post) is used to affix each end of the tissue graft to the bone.

In another example, a soft tissue may be anchored to passages in the femur and patella to reconstruct the medial patellofemoral ligament. Other examples of ligament reconstructions include, but are not limited to, elbow and ankle ligament reconstructions. Tendons not part of a ligament reconstruction may also be anchored into bone passages. An example is fixation of the proximal biceps tendon to the proximal humerus.

There remains a need for a soft tissue anchor and instrumentation for use with the anchor which is simple, easy to install, and inexpensive to manufacture, while providing secure, trouble-free anchoring of a soft tissue graft.

SUMMARY

In an aspect, the present disclosure relates to a soft tissue graft anchor. The anchor includes a plurality of prongs, each prong including a distal end and a proximal end, wherein the prongs are coupled at their distal ends to form an inner cavity having an opening, at least one of the prongs including a fin, the fin extending perpendicular to a longitudinal axis of the prong and including a pointed end. In an embodiment, at least one of the prongs includes at least one barb on at least one side surface of the prong. In another embodiment, the anchor includes a through hole, wherein the cavity extends into the through hole. In yet another embodiment, at least one of the prongs includes at least one groove.

In another aspect, the present disclosure relates to tissue graft anchor assembly. The anchor assembly includes a tissue graft anchor including a plurality of prongs, each prong including a distal end and a proximal end, wherein the prongs are coupled at their distal ends to form an inner cavity having an opening, at least one of the prongs including a fin, the fin extending perpendicular to a longitudinal axis of the prong and including a pointed end; and a fixation member configured to be disposed within the cavity.

In yet another aspect, the present disclosure relates to a method of tissue repair. The method includes creating a tunnel in bone; inserting a soft tissue graft within the tunnel; inserting a tissue graft anchor within the tunnel, the tissue graft anchor comprising a plurality of prongs, each prong including a distal end and a proximal end, wherein the prongs are coupled at their distal ends to form an inner cavity having an opening, at least one of the prongs including a fin, the fin extending perpendicular to a longitudinal axis of the prong and including a pointed end; and inserting a fixation member within the cavity of the tissue graft anchor, whereby inserting the fixation member into the cavity causes the prongs to twist and expand, thereby causing ends of the grafts to engage a wall of the tunnel and fixate the grafts to the bone.

In a further aspect, the present disclosure relates to a tension device. The tension device includes a body including two sides, wherein each side includes one wheel and two guides, wherein the wheel is configured for longitudinal movement relative to the body and the guides are stationary; a shoulder assembly coupled to the body; and a shaft assembly coupled to the shoulder assembly, the shaft assembly comprising a shaft and a handle coupled to the shaft, the handle including a window.

In yet a further aspect, the present disclosure relates to a broach. The broach includes a handle; and a shaft coupled to the handle, the shaft including a member located at an end of the shaft, the member including prongs, grooves located between the prongs, and a fin on at least one of the prongs, the fin extending perpendicular to a longitudinal axis of the of the prong.

In an aspect, the present disclosure relates to a delivery device. The delivery device includes a handle; a shaft coupled to the handle; and a movable member coupled to the shaft, the member including a track, a nipple coupled to the shaft located within the track, wherein the nipple is located in a first area of the track when the movable member is located in a first position and the nipple is located in a second area of the track when the movable member is located in a second position.

In another aspect, the present disclosure relates to a kit. The kit includes a tissue graft anchor including a plurality of prongs, each prong including a distal end and a proximal end, wherein the prongs are coupled at their distal ends to form an inner cavity having an opening, at least one of the prongs including a fin, the fin extending perpendicular to a longitudinal axis of the prong and including a pointed end; and a fixation member configured to be disposed within the cavity.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
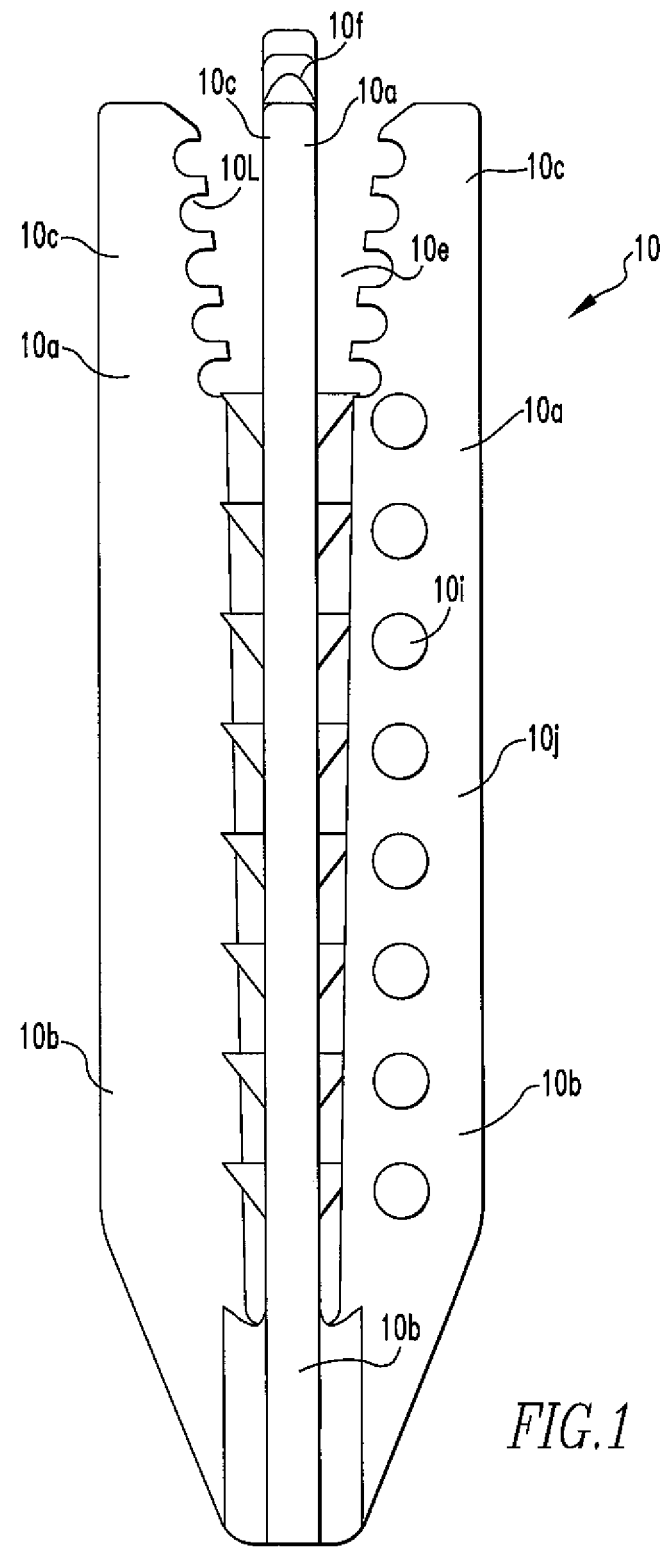
FIGS. 1 and 2 show side elevation views of the tissue graft anchor of the present disclosure.
Figure 2:
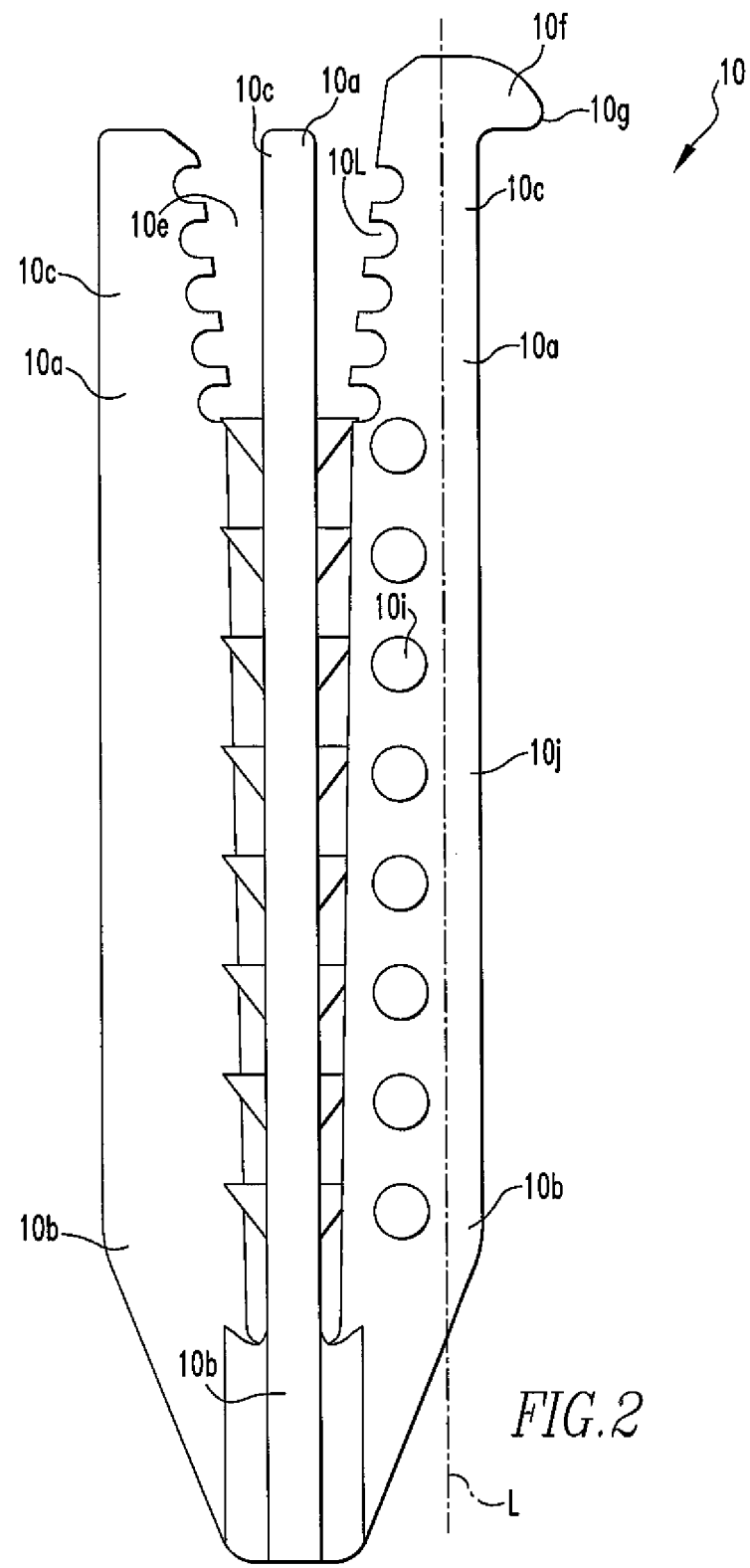
Figure 3:
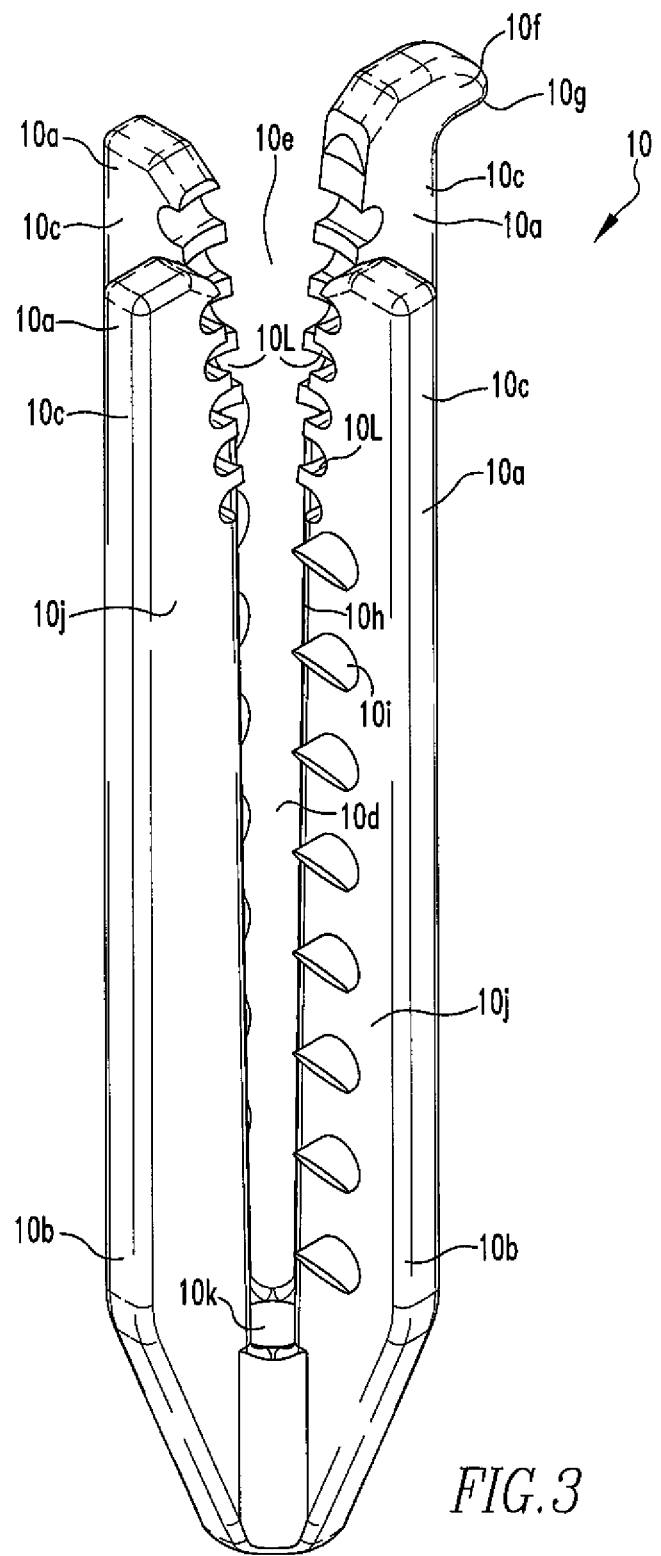
FIG. 3 shows an isometric view of the tissue graft anchor of the present disclosure.
Figure 4:
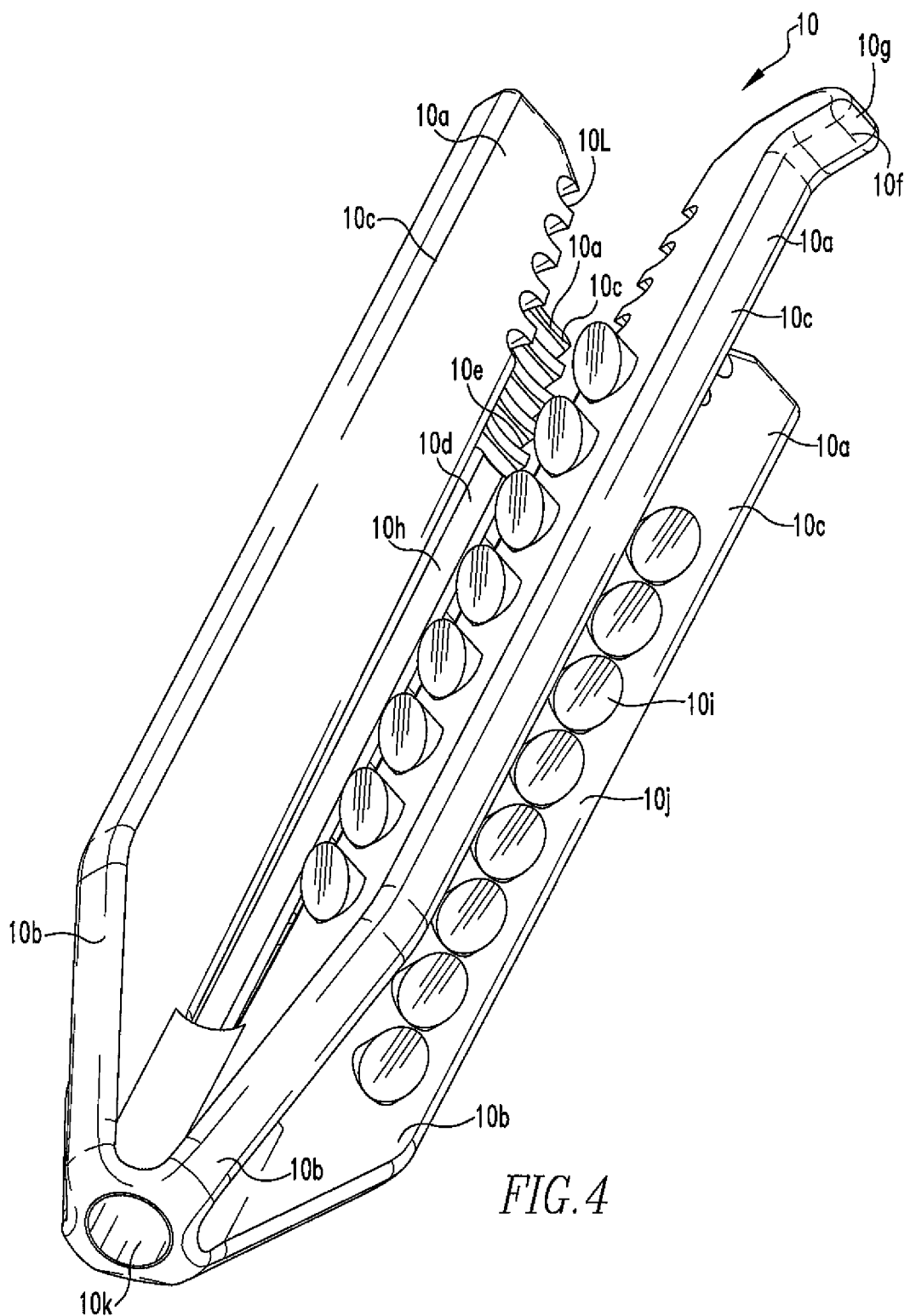
FIG. 4 shows an isometric view of the tissue graft anchor of the present disclosure.

FIGS. 1-4 show the soft tissue graft anchor 10 of the present disclosure. The anchor 10 includes prongs 10a, wherein each prong 10a has a distal end 10b and a proximal end 10c. The prongs 10a are coupled at their distal ends 10b to form an inner cavity 10d having an opening 10e and at least one prong 10a includes at least one barb 10i on at least one side surface 10j of the prong 10a. As shown in FIGS. 1-4, the number of prongs 10a having barbs 10i and the number of barbs 10i may vary. It is also within the scope of this disclosure for the prongs 10a to not have any barbs 10i. In addition, at least one of the prongs 10a includes a fin 10f. The fin 10f extends perpendicular to a longitudinal axis L of prong 10a and includes a pointed end 10g. An anchor 10 having prongs 10a wherein more than one prong 10a has a fin 10f and an anchor 10 without a fin 10f are also within the scope of this disclosure. For the purposes of the present disclosure, the tissue graft anchor 10 includes a plurality of prongs 10a, with the word plurality meaning at least two prongs 10a. Additionally, the anchor 10 includes a through hole 10k. However, it is within the scope of this disclosure for the anchor 10 to not include a through hole 10k. As shown in FIGS. 3 and 4, the inner cavity 10d extends into the through hole 10k.

Figure 5:
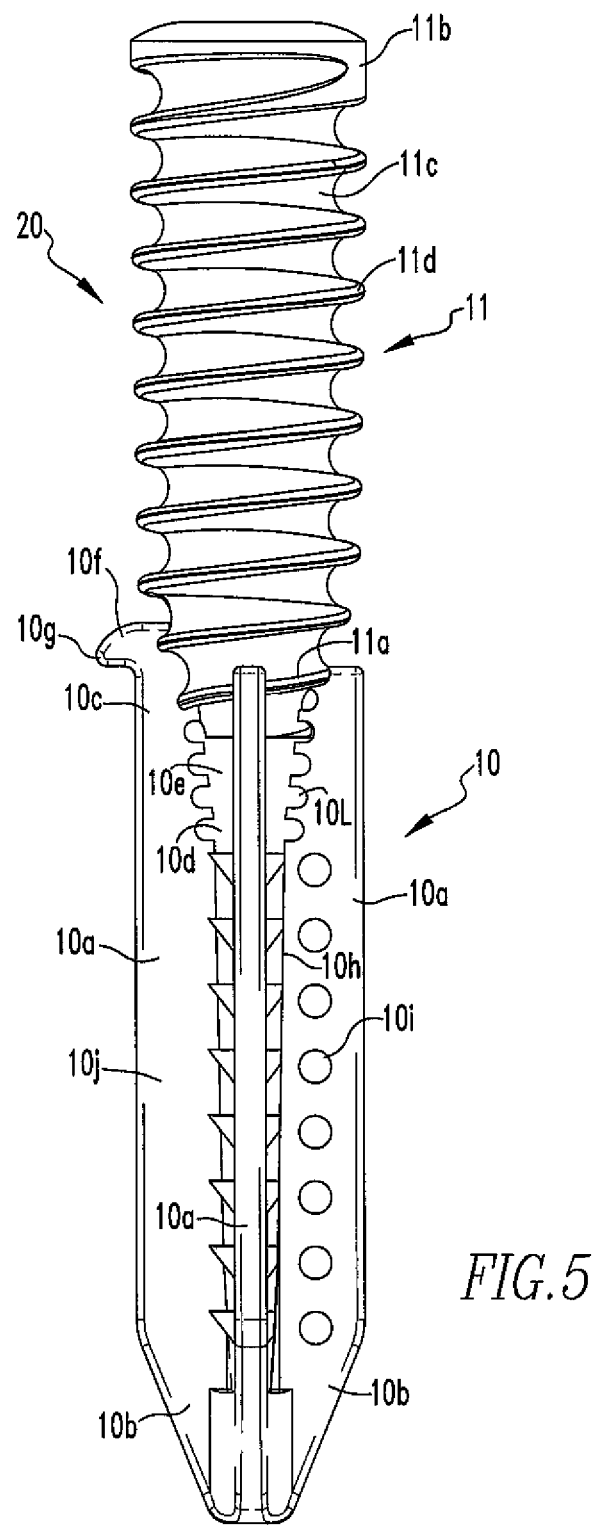
FIG. 5 shows a side elevation view of the tissue anchor assembly of the present disclosure.

FIG. 5 shows the tissue graft anchor assembly 20 of the present disclosure. The assembly 20 includes the tissue graft anchor 10 and a fixation member 11, which is configured to be disposed within the cavity 10d of the anchor 10. The fixation member 11 includes a distal end 11a, a proximal end 11b, and an outer surface 11c including threads 11d. The proximal end 11b includes a hole (not shown) that is configured for engagement with a delivery device (not shown) during surgery, as will be further described below. The hole may extend a partial length or a full length of the member 11. At least one of the prongs 10a also includes an inner surface 10h having at least one groove 10L that is configured for engagement with the threads 11d of the fixation member 11 upon insertion of the fixation member 11 into the inner cavity 10d, as will be further described below. As shown in FIGS. 1-4, the number of prongs 10a having grooves 10L and the number of grooves 10L may vary. For the purposes of this disclosure, the grooves 10L are located at the proximal ends 10c of the prongs 10a and extend a partial length of the prongs 10a, but may be located any where along the inner surface 10h, including along the entire inner surface 10h of the prongs 10a. It is also within the scope of this disclosure for the prongs 10a to not have any grooves 10L. Also, the inner surfaces 10h of proximal ends 10c of the prongs 10a are tapered along partial lengths of the inner surfaces 10h.

Figure 6:
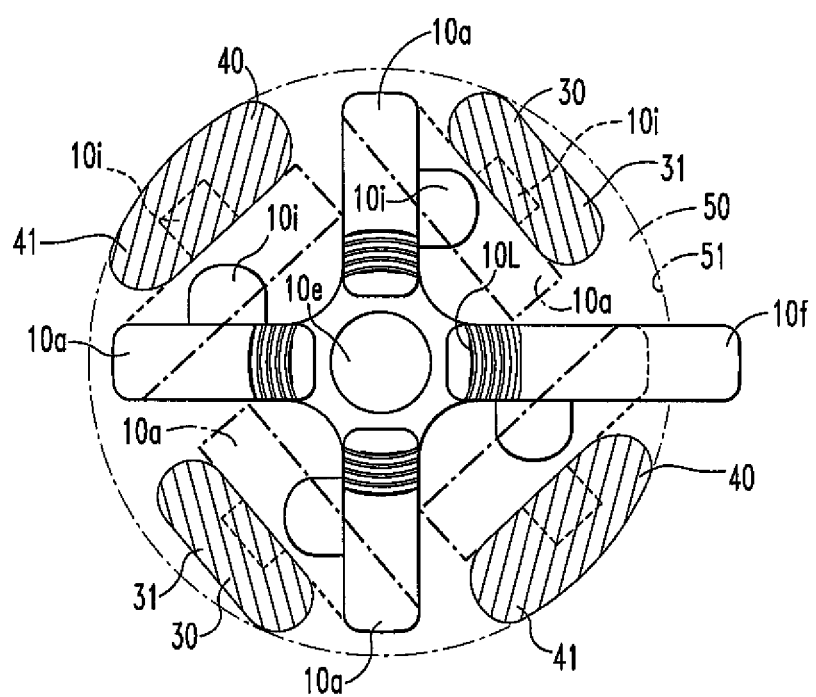
FIG. 6 shows the tissue graft anchor assembly of the present disclosure after insertion of the assembly into a bone tunnel.

As mentioned above, during ligament reconstruction surgery, tunnels are created in the femur and tibia and the replacement tissue graft is implanted by securing one end of the tissue graft in the tunnel formed within the femur and the other end of the graft in the tunnel formed within the tibia. One or more replacement tissue grafts may be used. FIG. 6 illustrates use of the assembly 20 to secure the ends 31,41 of the replacement grafts 30,40 within the tibial tunnel 50. Once the ends 31,41 are passed through the tunnel 50, the tissue anchor 10 is inserted into the tunnel 50 such that the ends 31,41 are located between the prongs 10a. The anchor 10 is seated within the tunnel 50 such that the prong 10a with the fin 10f is not completely inserted into the tunnel 50. Rather, as shown in FIG. 6, the fin 10f engages a portion of the tibia (outer surface of the tibia) outside of the tunnel and acts as a depth stop to substantially reduce over insertion of the anchor 10 into the tunnel 50. In addition to acting as a depth stop, the fin 10f engages the bone and allows for cortical fixation of the anchor 10.

The fixation member 11 is then inserted within the cavity 10d of the anchor 10 in a rotary manner. As mentioned above, the grooves 10i are configured for engagement with the threads 11d of the fixation member 11 to facilitate insertion of the fixation member 11 into the inner cavity 10d. In addition, the tapered inner surfaces 10h at the proximal ends 10c of the prongs 10a cooperate with the tapered distal portion 11a of the fixation member 11 to allow for easier insertion of the fixation member 11. During insertion of the fixation member 11 into the cavity 10d, the prongs 10a are caused to twist and expand, as shown in FIG. 6, thereby forcing the ends 31,41 of the grafts 30,40 against a wall 51 of the bone tunnel 50 and fixating the grafts 30,40 to the tibia. Additionally, upon insertion of the anchor 10 into the bone tunnel 50, the barbs 10i engage the ends 31,41 of the grafts 30,40 and apply compression to the ends 31,41 when the fixation member 11 is inserted into the inner cavity 10d so as to further fixate the grafts 30,40 to the tibia.

For the purposes of this disclosure, the fixation member 11 is not shown in FIG. 6. However, the illustration in FIG. 6 and the following corresponding description describes insertion of the fixation member 11 into the inner cavity 10d and subsequent fixation of the grafts 30,40 to bone as if the member 11 was shown in FIG. 6. The anchor 10 is made from a non-metal material, including, but not limited to a polymer material. However, it may be made from a metal material. Also, the anchor 10 is made via an injection molding process, but may be made via another process known to one of skill in the art. The fixation member 11 is made from a non-metal material, including, but not limited to a polymer material and is made via an injection molding process. However, other materials and processes known to one of skill in the art are also possible.

For the purposes of this disclosure, the assembly 20 is used to fixate soft tissue within the tibial tunnel. However, the assembly 20 may be used to fixate soft tissue within the femoral tunnel or to bone in other parts of the body, such as described above in other types of ligament reconstructions and procedures. In addition, the assembly may be used to fixate soft tissue to bone in other areas of the body. The method described above may further include locating a guide wire within the femoral and tibial tunnels either before or after the tunnels are drilled for guiding the drill and/or guiding placement of the anchor 10 and/or the fixation member 11 within the tunnel.

Figure 7:
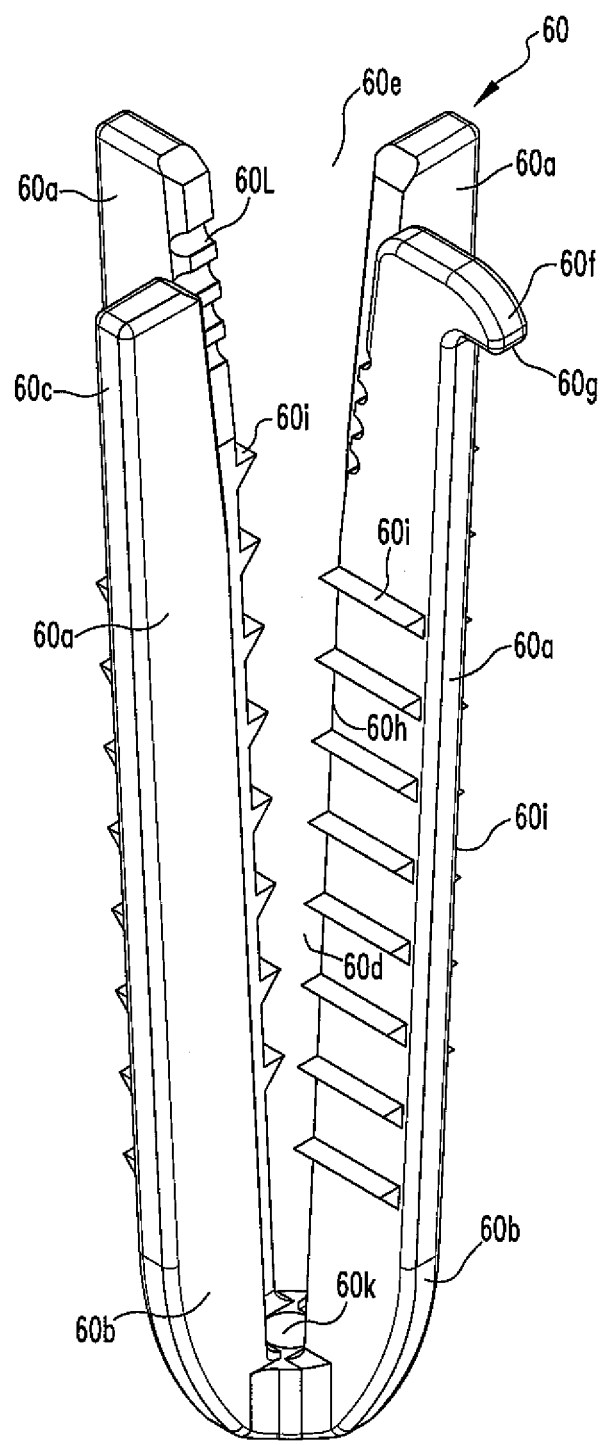
FIG. 7 shows an isometric view of an alternative embodiment of the tissue graft anchor of the present disclosure.
Figure 8:
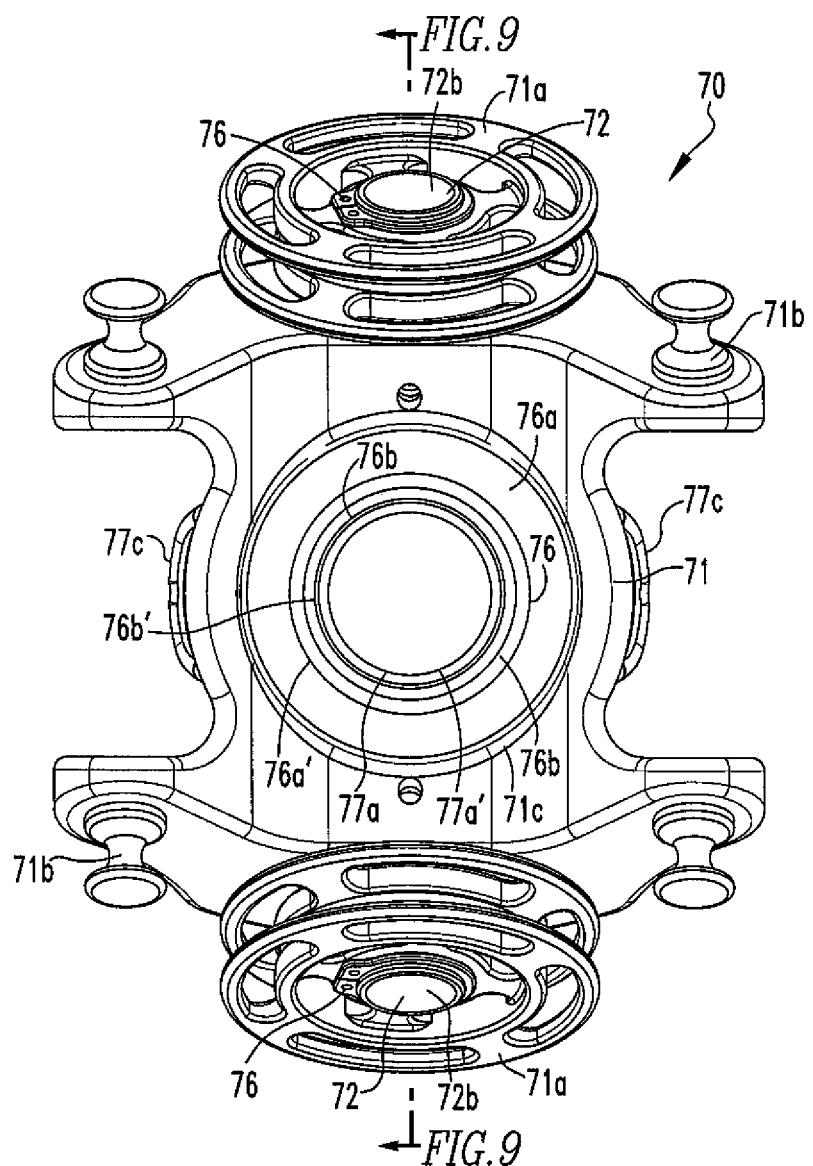
FIGS. 8-11 show the tension device of the present disclosure and its components.
Figure 9:
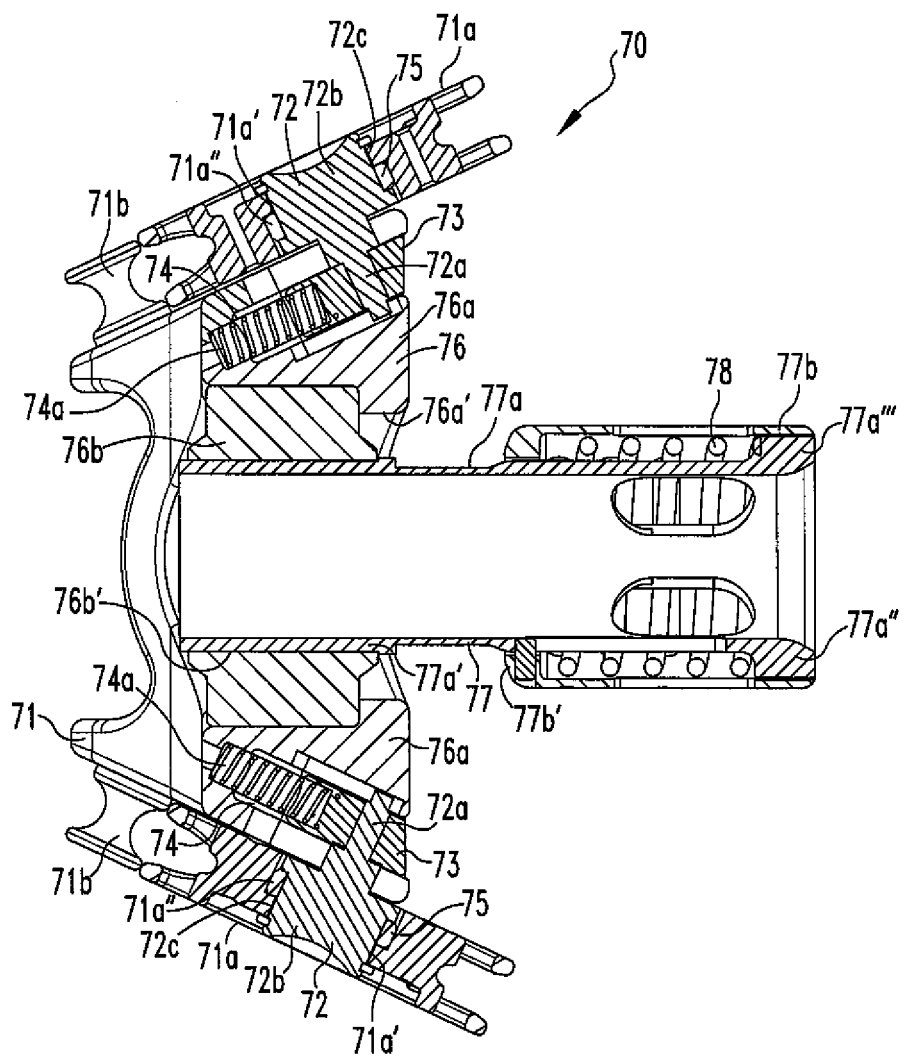
Figure 10:
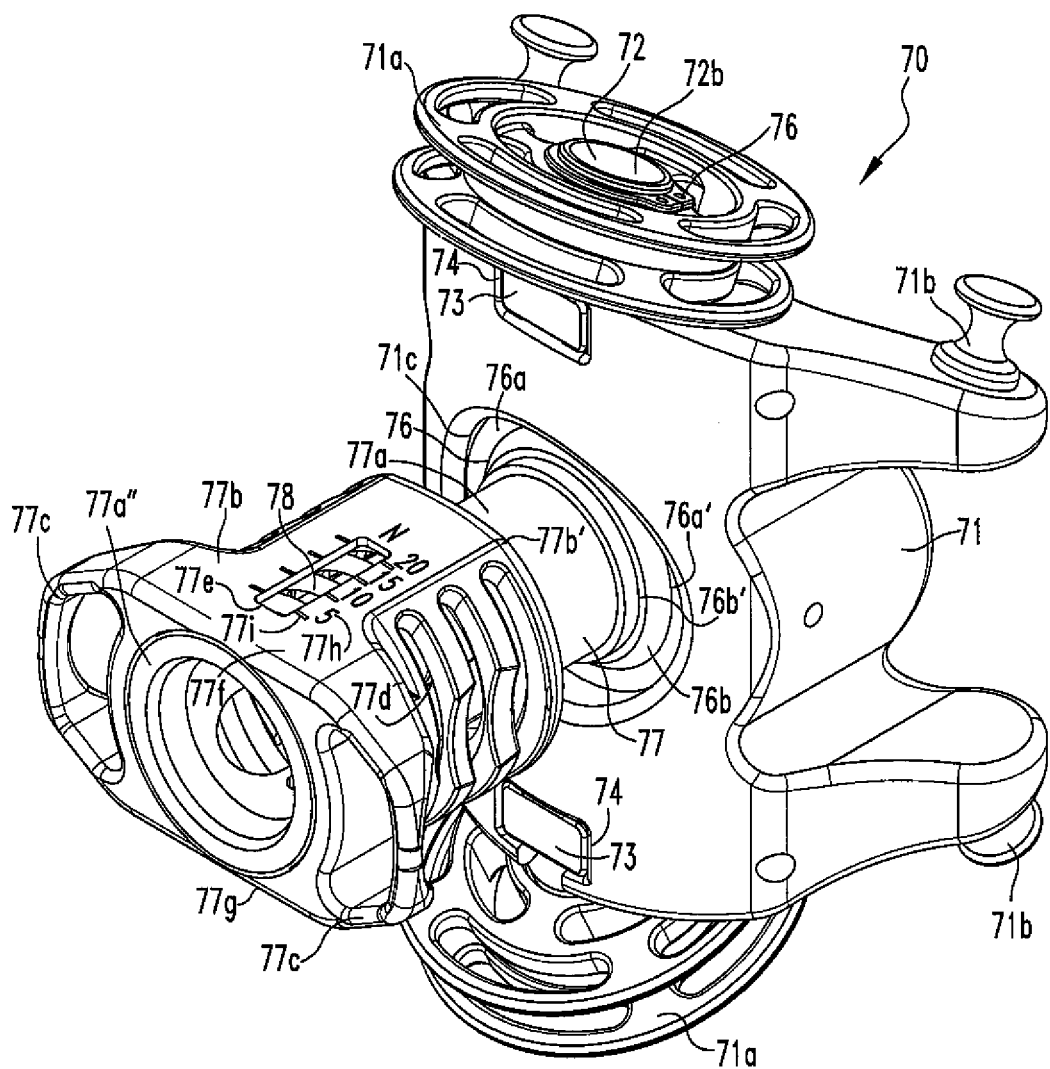

FIG. 7 shows an alternative embodiment of the tissue graft anchor 60 of the present disclosure. Anchor 60 is similar to anchor 10. However, anchor 60 differs from anchor 10 such that the distal ends 60b of the prongs 60a are substantially rounded, rather than tapered; the barbs 60i are wider and straight compared to barbs 10i, and only two of the prongs 60a have grooves 60L, rather than four, as in anchor 10.

FIGS. 8-15 show instrumentation for use with anchors 10,60 during ligament reconstruction surgery. FIGS. 8-11 show a tension device 70 for applying tension to a soft tissue graft prior to fixating the soft tissue graft to bone via use of one of anchors 10,60. The device 70 includes a body 71 having suture wheels 71a and guides 71b. For the purposes of this disclosure, each side of the body 71 includes one wheel 71a and two guides 71b. However, the number of wheels 71a and guides 71b may vary. The guides 71b are stationary, but the wheels 71a are capable of being rotated and moved longitudinally relative to the body 71. Each wheel 71a has a central opening 71a' through which is disposed a bearing pin 72. A first end 72a of each bearing pin 72 is coupled to a movable insert 73, which is housed within a slot 74.

Springs 74a are also located within slots 74 to allow for longitudinal movement of the inserts 73, and thus the wheels 71a, when tension is applied via use of the tension device 70, as will be further described later. The wheels 71a are located on second ends 72b of the bearing pins 72 such that first snap rings 75 are located between the wheels 71a and the second ends 72b of the bearing pins 72. The snap rings 75 may be coupled to outer surfaces 72c of the bearing pins 72 or inner surfaces 71a" of the wheel openings 71a'.

The device 70 also includes a central opening 71c to which a shoulder assembly 76 is coupled. The assembly 76 includes a shoulder 76a disposed within the opening 71c and a bearing 76b coupled to the shoulder 76a. The shoulder 76a has a central opening 76a', in which the bearing 76b is disposed, and the bearing 76b has a central opening 76b'. A shaft assembly 77 is coupled to the shoulder assembly 76. The shaft assembly 77 includes a shaft 77a and a handle 77b coupled to the shaft 77a. The shaft 77a includes a first end 77a' and a second end 77a". The first end 77a' is coupled to the shoulder assembly 76 such that the first end 77a' is disposed within the bearing central opening 76b'. The second end 77a" of the shaft 77a includes a flange 77a''', the purposes of which will be described later.

Figure 11:
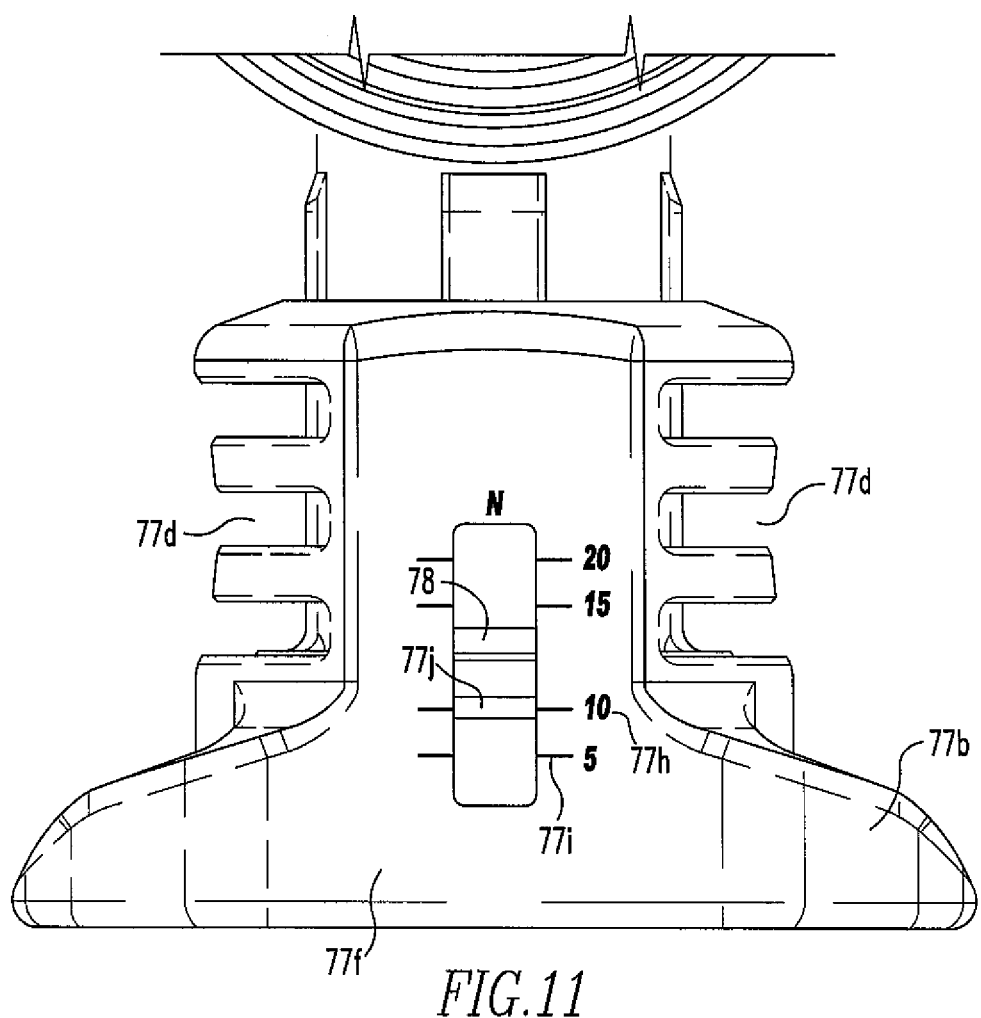

Located on the shaft 77a is a cannulated handle 77b. Also disposed on the shaft 77a is a spring 78 located between an end 77b' of the handle 77b and the flange 77a'''. The handle 77b includes pull members 77c, grooves 77d, a first window 77e on a first side 77f of the handle 77b, and a second window (not shown) on a second side 77g of the handle 77b. Sets of reference numbers 77h are located next to each window and a hash mark 77i corresponds with each reference number. The reference numbers 77h refer to the amount of tension applied by the user in Newtons (first side) or pounds (second side). During reconstruction surgery, force is applied to the handle 77b by pulling the handle 77b toward the user until a hash mark 77j, located on the second end 77a" and visible through the window 77e, is in line with a hash mark 77l that represents the amount of tension required by the user, as shown in FIG. 11 and as will be further described below. During this time, when the user is pulling on the handle 77b, the spring 78 is in a compressed state.

For the purposes of this disclosure, the shoulder 76a is press-fit into the opening 71c, the bearing 76b is press-fit into the opening 76a' of the shoulder 76a, the shaft 77a is press-fit and welded into the opening 76b' of the bearing 76b, and the first end 72a of the bearing pin 72 is press-fit into the insert 73. However, other method of coupling may also be used.

Figure 12:
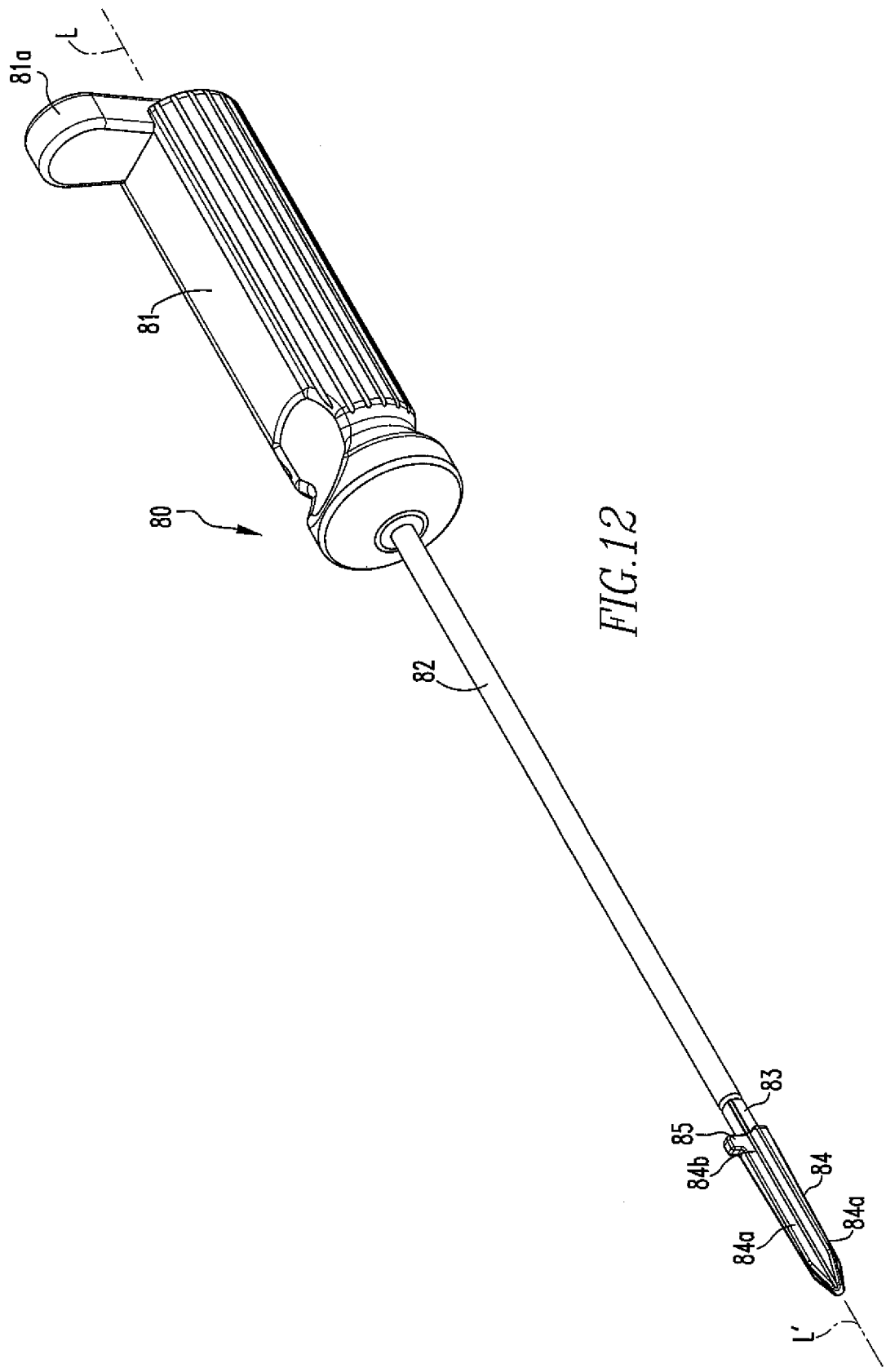
FIG. 12 shows an isometric view of the broach of the present disclosure.

FIG. 12 shows a cannulated broach 80 for use during reconstruction surgery. The broach 80 is used to divide the ends of the tissue grafts and create a seat for the anchor 10,60, as will be further described below. The broach 80 includes a handle 81 and a shaft 82 coupled to the handle 81. The handle 81 includes a removal tab 81a extending perpendicular to a longitudinal axis L of the handle 81. The shaft 82 includes a member 84 located at an end 83 of the shaft 82. The member 84 is similar to the anchors 10,60 in that the member 84 has prongs 84a and grooves 84b located between the prongs 84a. Similarly, at least one of the prongs 84a includes a fin 85 extending perpendicular to a longitudinal axis L' of the prong 84a.

Figure 13:
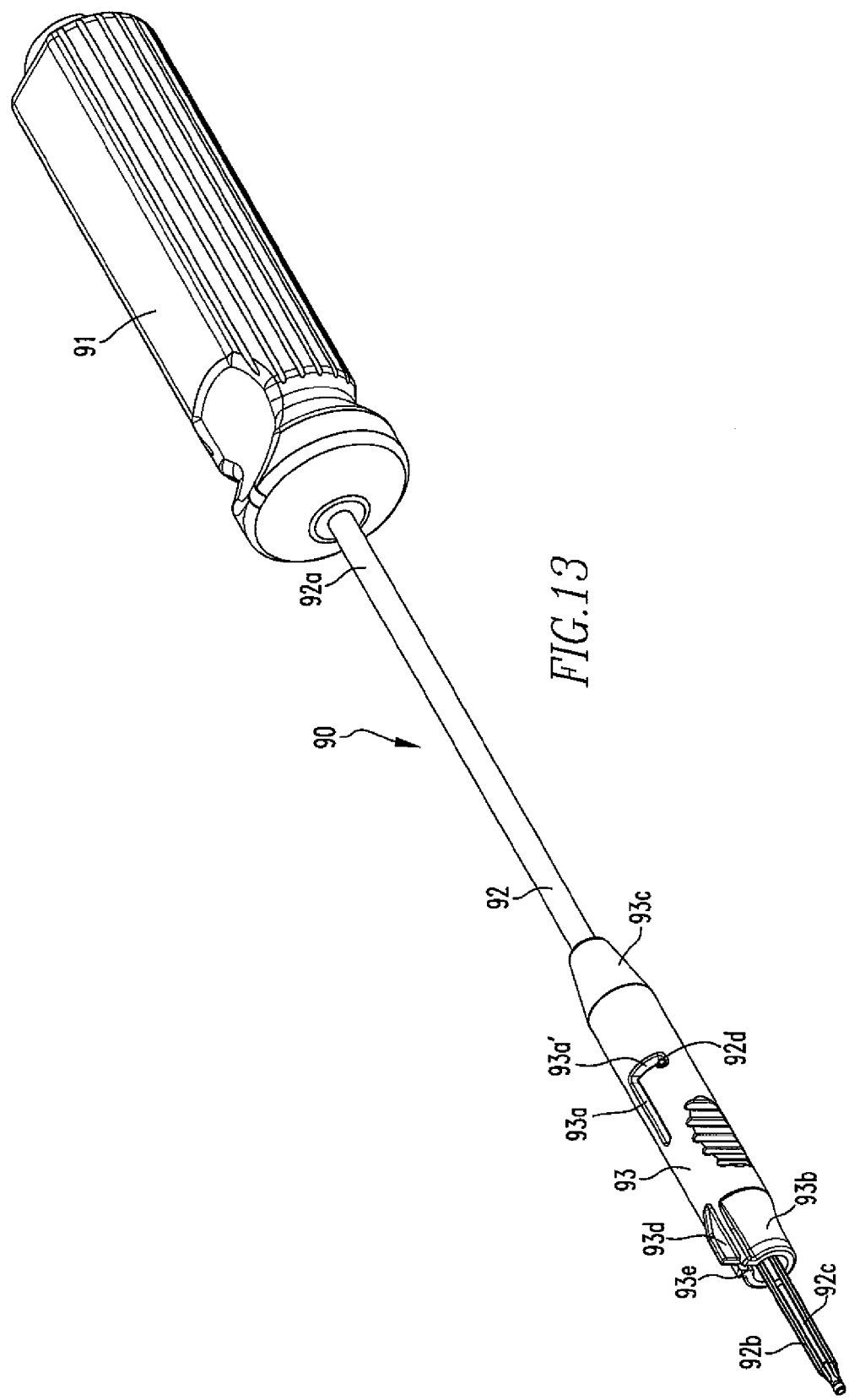
FIGS. 13-15 show the delivery device of the present disclosure.
Figure 14:
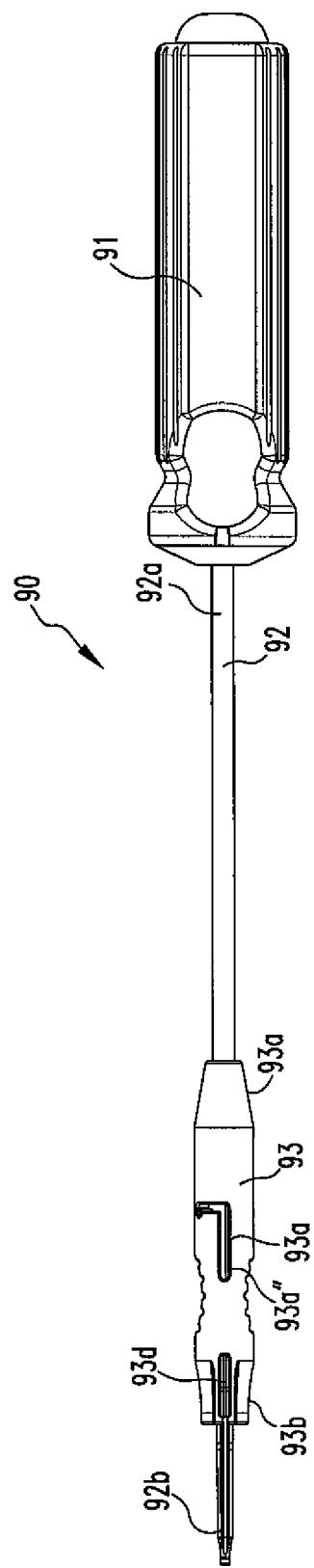
Figure 15:
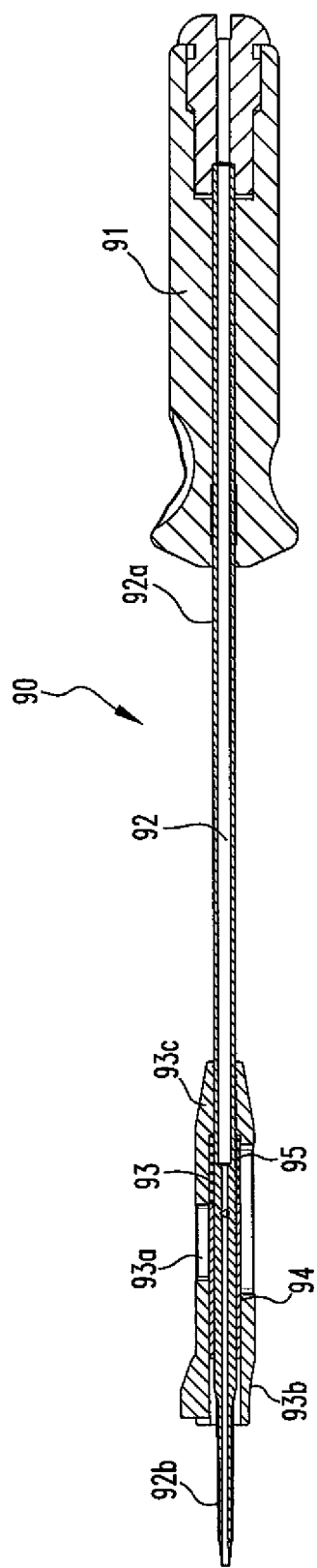

FIGS. 13-15 show a cannulated delivery device 90 for use in delivering the anchors 10,60. The device 90 includes a handle 91, a shaft 92 coupled to the handle 91, and a movable member 93 coupled to the shaft 92. Also coupled to the shaft 92 and located between the movable member 93 and the shaft 92 are a fixed spring stop 94 and a spring 95. The shaft 92 includes a proximal end 92a and a distal end 92b. The distal end 92b includes a plurality of longitudinal grooves 92c that extend a partial length of the shaft 92. The movable member 93 includes a track 93a through which a nipple 92d, coupled to the shaft 92, rides in. In a first position, the nipple 92d is located, in a first area 93a' of the track 93a, as shown in FIG. 13, and in a second, retracted position the nipple 92d is located in a second area 93a" of the track 93a. The movable member 93 also includes a distal portion 93b and a proximal portion 93c. The distal portion 93b includes a fin 93d and an opening 93e. When the anchor 10,60 is located on the distal end 92b of the shaft 92, fin 10f,60f is disposed within the opening 93e and aligned with fin 93d. In the first and second positions, as described above, the spring 95 is in a relaxed position and a compressed position, respectively. When the movable member is in the second position, the spring 95 is compressed between the proximal portion 93c and the spring stop 94.

Figure 16:
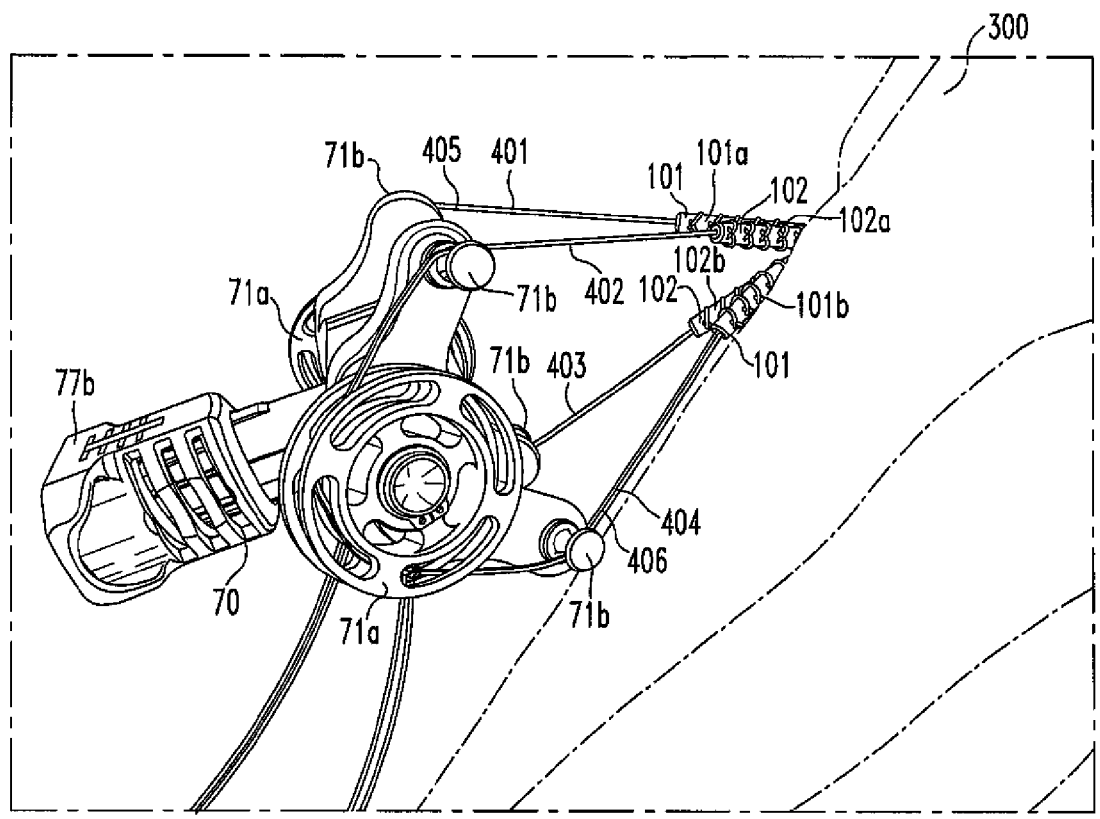
FIGS. 16, 16A, 17, 17A, 18, 18A, 19 and 19A show soft tissue reconstruction surgery via use of the tissue graft anchors of the present disclosure.
Figure 16A:
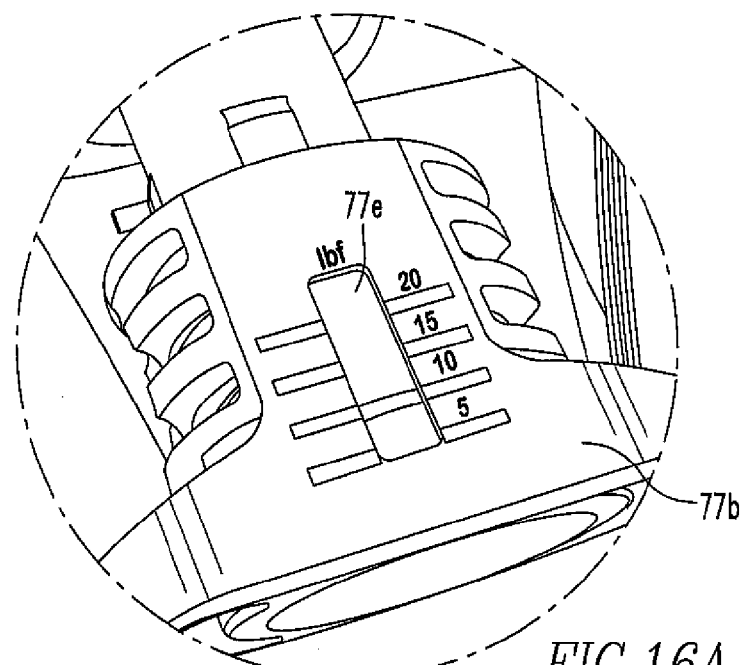

As shown in FIG. 16, once the replacement tissue grafts 101,102 are secured in the femur (not shown) and the ends 101a-b,102a-b of the grafts 101,102 are located in the tibial tunnel 301, suture 401-404 coupled to the ends 101a-b, 102a-b are formed into two loops 405,406. For the purposes of this disclosure, two grafts 101,102 are used. However, the use of more or less than two grafts is also within the scope of this disclosure. Each graft 101,102 has two ends 101a-b, 102a-b and a suture 401-404 extends from each end 101a-b, 102a-b, such that two suture ends 401,403 are tied together to form a first loop 405 and the other two suture ends 402,404 are tied together to form a second loop 406. Subsequently, the first loop 405 is placed around a wheel 71a and two suture guides 71b on one side of the tension device 70 and the second loop 406 is placed around a wheel 71a and two suture guides 71b on the other side of the tension device 70. The handle 77b is then pulled towards the user until the proper amount of tension is shown in the window 77e, as shown in FIG. 16A.

Figure 17:
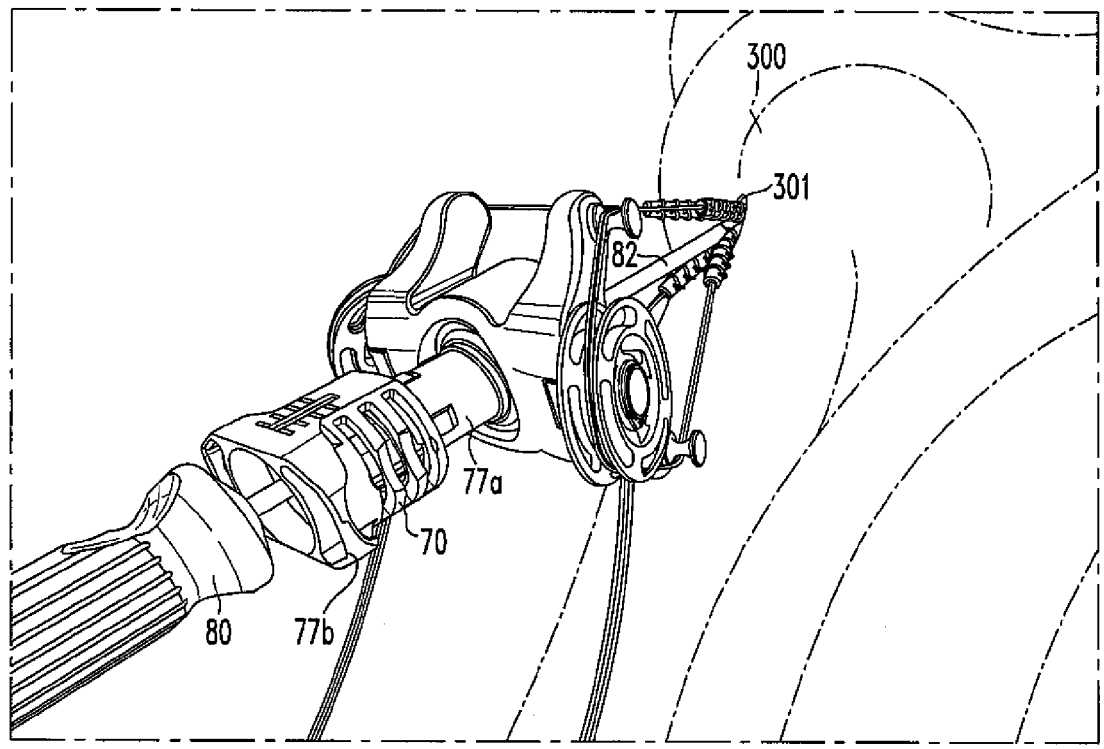
Figure 17A:
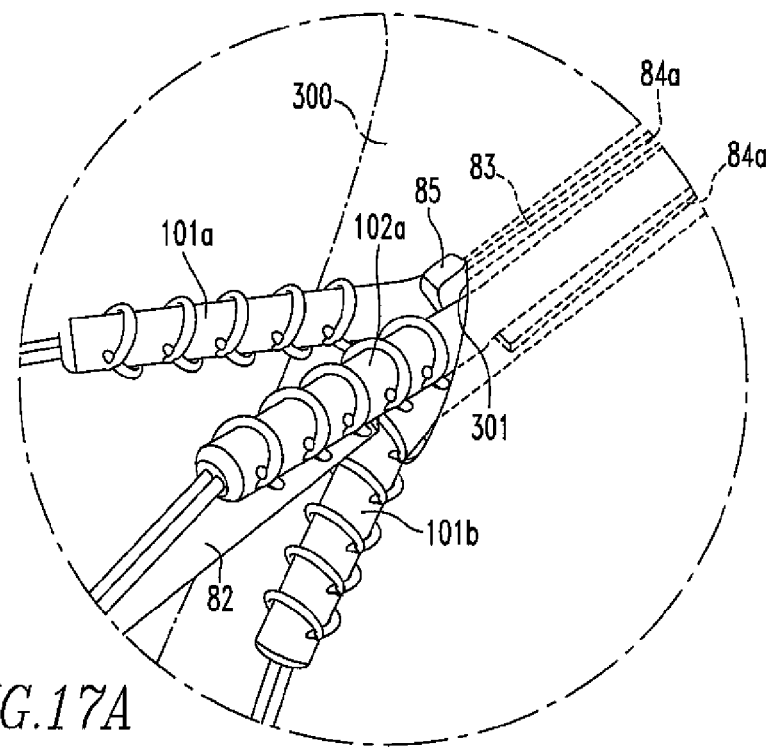

A guide wire (500, FIG. 19) is then placed in the tunnel 301. As shown in FIG. 17, the shaft 82 of the broach 80 is then placed over the guide wire 500, through the tension device 70, via the cannulated handle 77b and shaft 77a, and the end 83 is placed within the tibial tunnel 301 such that the prongs 84a are inserted between the ends 101a-b,102a-b of the soft tissue grafts 101,102 to divide the grafts 101,102, as shown in FIG. 17A. As the prongs 84a extend between the grafts 101,102, they also extend into the wall of the tibial tunnel 301 to create a seat for the prongs 10a,60a of the anchor 10,60 when the anchor 10,60 is inserted into the tunnel 301. The fin 85 of the broach 80 engages a portion of the tibia 300 outside of the tunnel 301 and acts as a depth stop to substantially reduce over insertion of the end 83 of the broach 80 into the tunnel 301, as also shown in FIG. 17A.

Figure 18:
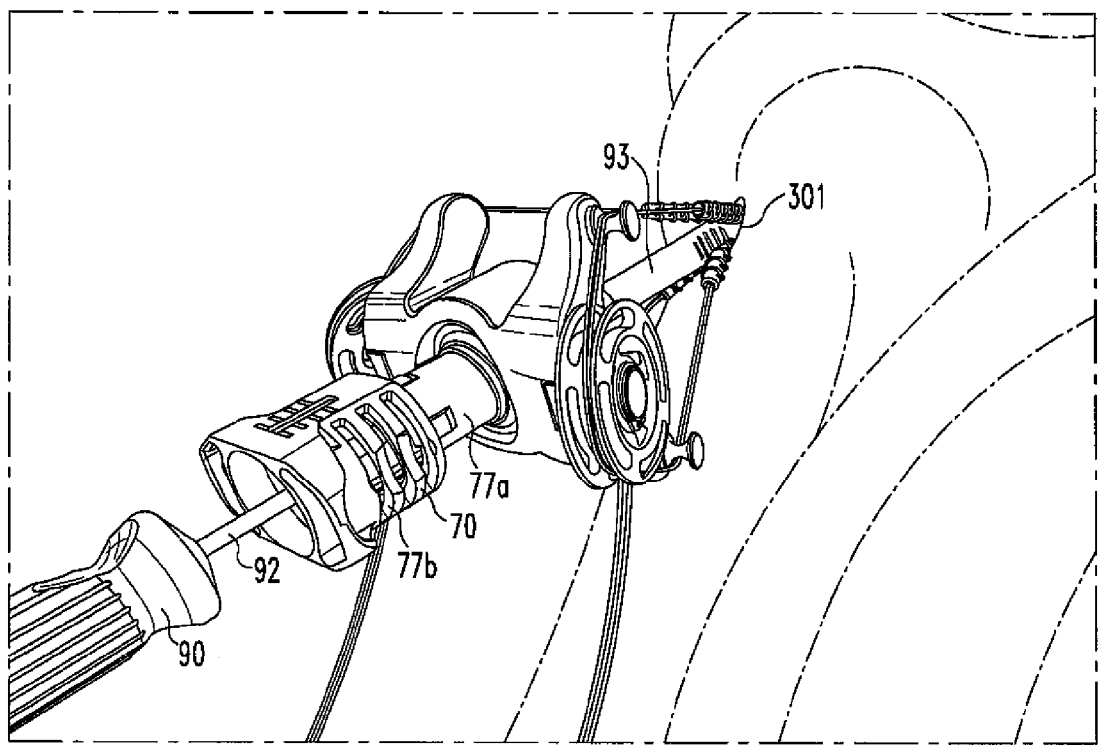
Figure 18A:
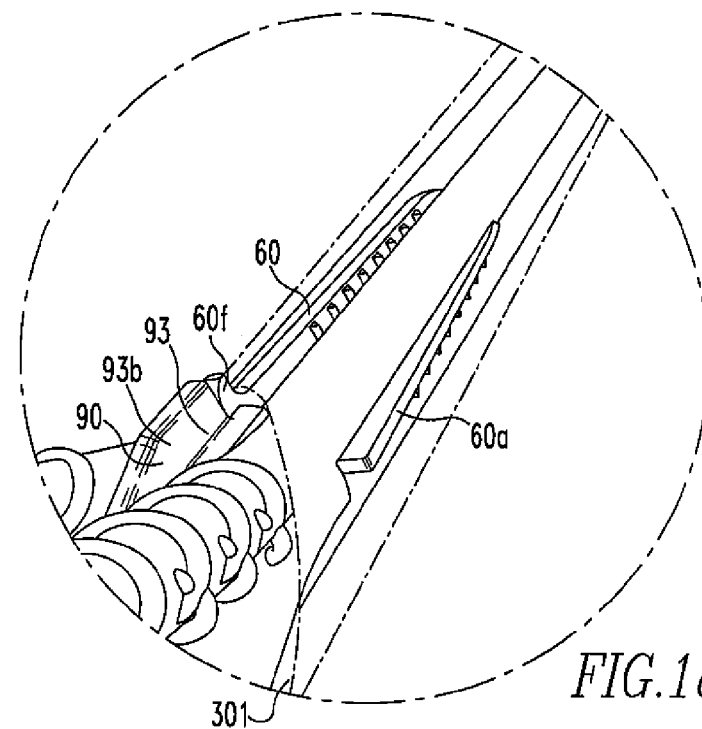
Figure 19:
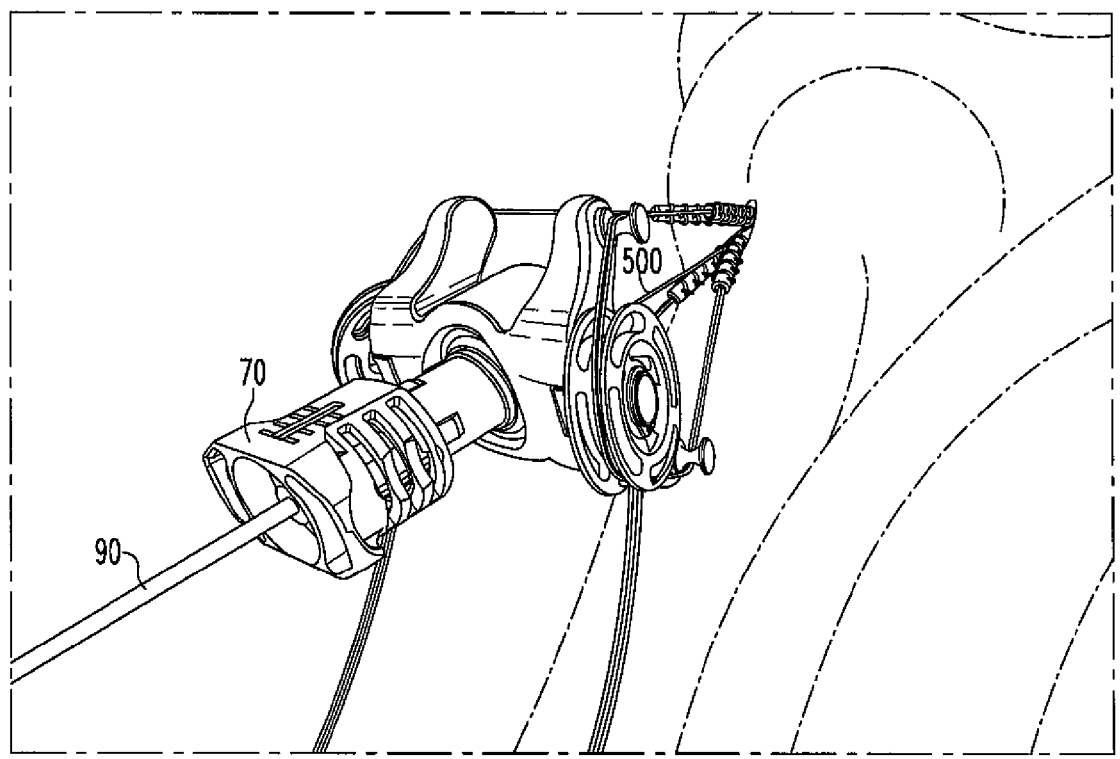
Figure 19A:
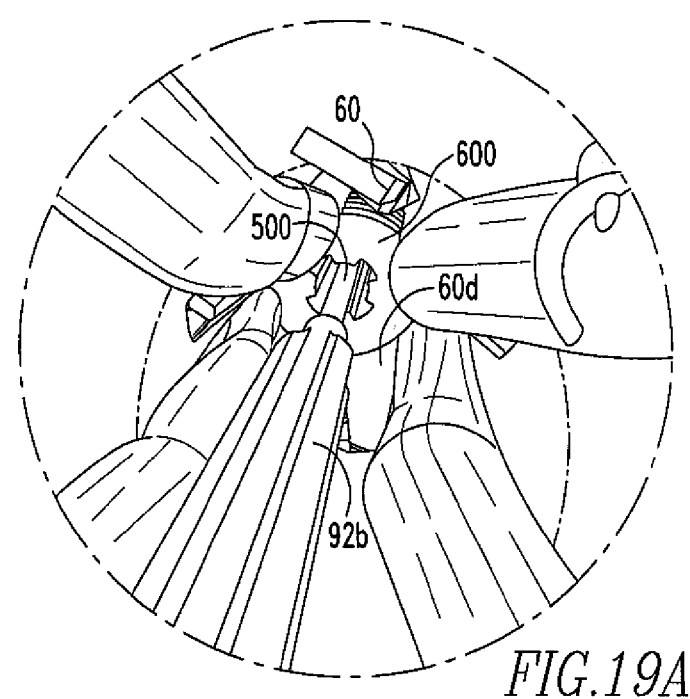

The anchor 10,60 is then loaded on the distal end 92b of the delivery device 90, while the delivery device is in the first position, as described above, by placing the distal end 92b of the delivery device 90 into the cavity 10d,60d of the anchor 10,60 such that the prongs 10a,60a engage the grooves 92c and the fin 10f,60f of the anchor 10,60 aligns with the fin 93d of the movable member 93 and is secured in the opening 93e. The shaft 92 of the delivery device 90 is inserted over the guide wire 500, through the tension device 70, via the cannulated handle 77b and shaft 77a, and the distal end 92b, and therefore the anchor 10,60, is placed into the tunnel 301 until the fin 10f,60f engages a portion of the tunnel 301, as described above and shown in FIGS. 18 and 18A. The delivery device 90 is then removed and the movable member 93 is retracted to place the movable member 93 in the second position, as described above. The fixation member 600 is then loaded onto the distal end 92b of the delivery device 90 and the device 90 is inserted through the tension device 70 and into the cavity 10d,60d of the anchor 10,60. The member 600 is inserted into the cavity 10d,60d as described and shown above in FIG. 6 and as also shown in FIGS. 19 and 19A. After the delivery device 90 is removed from the tunnel 301, the suture loops 405,406 are removed from the tension device 70 and the ends 101a-b,102a-b of the grafts 101,102 are cut.

Figure 20:
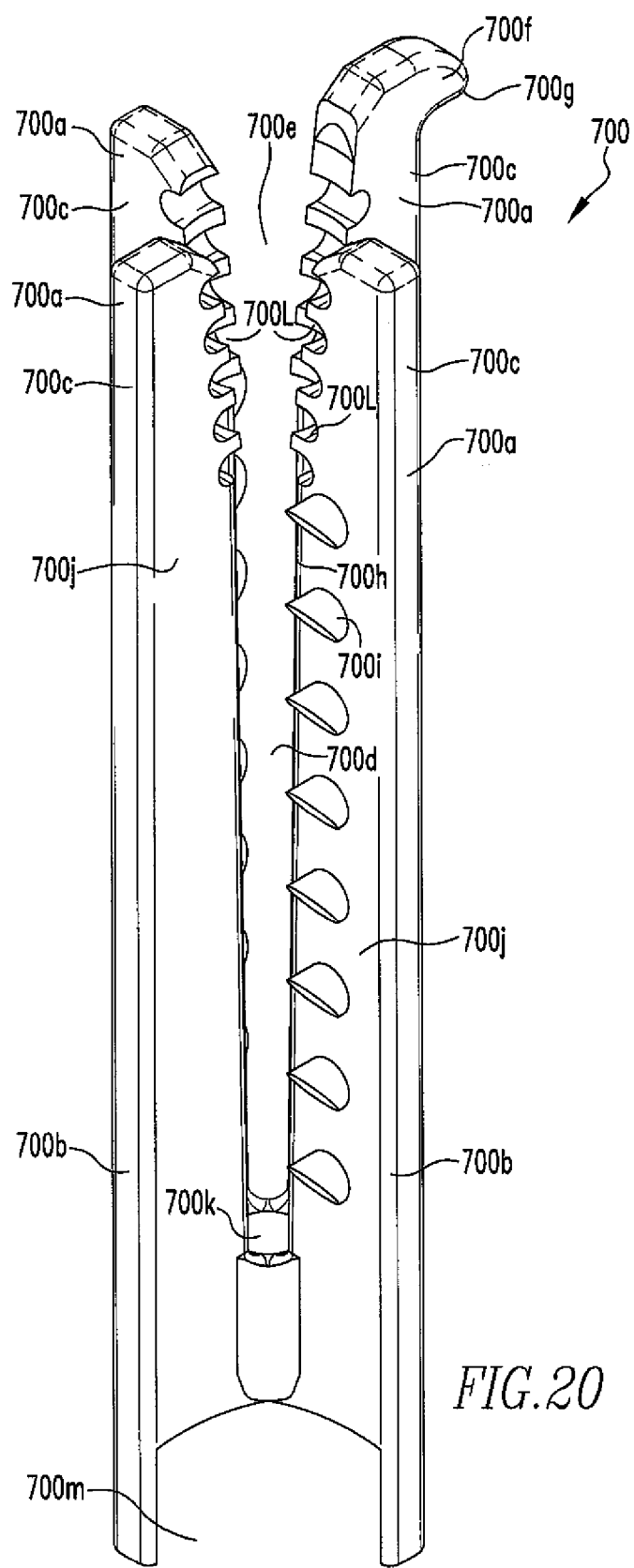
FIG. 20 shows an isometric view of another alternative embodiment of the tissue graft anchor of the present disclosure.

FIG. 20 shows another alternative embodiment of the anchor 700. Anchor 700 is similar to anchor 10. However, anchor 700 differs from anchor 10 such that the distal ends 700b of the prongs 700a are extended, rather than tapered, and spaces 700m exist between the extended portions. During use of the anchor 700 in surgery, one or more grafts may be extended over the anchor 700 such that the grafts are located within the grooves 700m and the ends of the grafts are located between the prongs 700a.

For the purposes of this disclosure, a guide wire is used during surgery. The guide wire is inserted into the tunnel and the instruments are inserted over the guide wire. However, it is possible for the guide wire to be inserted into the tunnel in other manners. It is also within the scope of this disclosure for the guide wire to not be used. In this instance, the anchor, fixation member, and instrumentation may be non-cannulated. Furthermore, it is within the scope of this disclosure for a tension device to not be used during surgery.

Additionally, it is within the scope of this disclosure for the anchors to have a varying number of prongs. Also, for the purposes of this disclosure the prongs are symmetric. However, the prongs may be asymmetric.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A tension device comprising:
   a body comprising two sides, wherein each side comprises one wheel and two guides, wherein the wheel is configured for longitudinal movement relative to the body and the guides are stationary;
   a shoulder assembly coupled to the body; and
   a shaft assembly coupled to the shoulder assembly, the shaft assembly comprising a shaft and a handle coupled to the shaft, the handle having a tension spring disposed within,
   the handle including a first window and a second window, wherein said windows have hash marks.

2. The tension device according to claim 1, wherein the wheel has a central opening through which is disposed a bearing pin having a first and second end.

3. The tension device according to claim 2, wherein the bearing pin is coupled to a movable insert that is housed within a slot.

4. The tension device according to claim 3, wherein a spring is located with the slot to allow for longitudinal movement of the insert and the wheel when tension is applied.

5. The tension device according to claim 4, wherein the wheel is located on second end of the bearing pin, wherein a first snap ring is located between the wheel and the second end of the bearing pin.

6. The tension device according to claim 1, further comprising a central opening to which the shoulder assembly is coupled.

7. The tension device according to claim 6, wherein the assembly includes a shoulder disposed within the opening and a hearing coupled to the shoulder.

8. The tension device according to claim 7, wherein the shoulder has a central opening in which the bearing is disposed and the bearing has a central opening.

9. The tension device according to claim 1, wherein the hash marks correspond with reference numbers correlating with tension.

10. The tension device according to claim 9, wherein the reference numbers correlate with to the amount of tension applied by the user.

11. The tension device according to claim 10, wherein the tension is measured by Newtons.

12. The tension device according to claim 10, wherein the tension is measured by pounds.

13. The tension device according to claim 10, wherein the tension is measured by pounds in the first window and by Newtons in the second window.

14. The tension device according to claim 1, wherein the spring is in a compressed state when tension is applied.

15. The tension device according to claim 1, wherein the body has at least two wheels on each side.

16. The tension device according to claim 1, wherein the wheels are configured to receive a suture.

17. The tension device according to claim 1, wherein the body has at least two guides on each side.

18. The tension device according to claim 1, wherein the wheels are configured to rotate.

19. The tension device according to claim 1, wherein the handle is cannulated.

20. The tension device according to claim 1, wherein the handle is removably attached to the body.

* * * * *